(12) United States Patent
Schulz et al.

(10) Patent No.: US 12,161,454 B2
(45) Date of Patent: Dec. 10, 2024

(54) SIGNAL TRANSMISSION FOR MAGNETIC-PARTICLE-IMAGE SIGNAL DETECTION

(71) Applicant: RHEINISCH-WESTFÄLISCHE TECHNISCHE HOCHSCHULE (RWTH) AACHEN, Aachen (DE)

(72) Inventors: Volkmar Schulz, Wuerselen (DE); Sebastian Reinartz, Hueckelhoven Baal (DE); Dennis Pantke, Cologne (DE); Florian Mueller, Aachen (DE)

(73) Assignee: RHEINISCH-WESTFAELISCHE-TECHNISCHE HOCHSCHULE (RWTH) AACHEN, Aachen (DE)

( * ) Notice: Subject to any disclaimer, the term of this patent is extended or adjusted under 35 U.S.C. 154(b) by 624 days.

(21) Appl. No.: 17/430,735

(22) PCT Filed: Mar. 13, 2020

(86) PCT No.: PCT/EP2020/056912
§ 371 (c)(1),
(2) Date: Aug. 13, 2021

(87) PCT Pub. No.: WO2020/187764
PCT Pub. Date: Sep. 24, 2020

(65) Prior Publication Data
US 2022/0167866 A1  Jun. 2, 2022

(30) Foreign Application Priority Data
Mar. 15, 2019 (DE) .................... 10 2019 106 665.4

(51) Int. Cl.
*G01N 27/84* (2006.01)
*A61B 5/0515* (2021.01)
*G01R 33/12* (2006.01)

(52) U.S. Cl.
CPC ........ *A61B 5/0515* (2013.01); *G01R 33/1276* (2013.01)

(58) Field of Classification Search
CPC ........ G01R 33/34; G01R 33/36; G01R 33/38; G01R 33/3804; G01R 33/381;
(Continued)

(56) References Cited

U.S. PATENT DOCUMENTS 7,282,915 B2 * 10/2007 Giaquinto .......... G01R 33/3415
324/318
7,747,304 B2   6/2010 Gleich
(Continued)

OTHER PUBLICATIONS

Borget, Joern "Fundamentals and application of magnetic particle imaging" Journal of Cardiovascular Computed Topography 2012.
(Continued)

*Primary Examiner* — Thang X Le
(74) *Attorney, Agent, or Firm* — Andrew Wilford

(57) ABSTRACT

The invention relates to a method for carrying out signal detection by means of magnetic particle imaging, in which method magnetic/magnetisable particles (4), arranged in the field-free region of a location-dependent magnetic field, in particular a gradient magnetic field, are magnetised by means of an excitation magnetic field that changes over time, and the harmonics (9, 15), generated by the particles (4), of the frequency of the excitation magnetic field are detected as a signal from the magnetic particles (4) by means of a receiver coil arrangement (1) which in particular surrounds the particles (4), wherein a signal-transmitting arrangement, which has an outer coil (10) and at least one inner coil (11; 16, 17) connected in series to said outer coil, is positioned within the receiver coil arrangement (1) around the particles (4), wherein the signal received from the particles (4) by the at least one inner coil (11; 16, 17) is transmitted to the outer coil (10) by current flow and is
(Continued)

re-emitted by said outer coil, in particular as a result of which the signal (S) received directly from the particles (4) and the signal (S) received from the particles (4) indirectly by the outer coil (10) are superimposed at the receiver coil arrangement (1). The invention also relates to a signal-transmitting arrangement for a magnetic-particle-imaging scanner/spectrometer, comprising an outer coil (10) which in particular has a smaller diameter than the sample-receiving channel (2) of the scanner/spectrometer, and comprising at least one inner coil (11; 16, 17) which is arranged in the outer coil (10), preferably arranged coaxially therein, and in particular has greater diameter than a sample to be examined, wherein the outer coil (10) and the inner coil (11; 16, 17) are electrically connected in series. The invention also relates to a system comprising a magnetic-particle-imaging scanner and a signal-transmitting arrangement.

16 Claims, 4 Drawing Sheets

(58) Field of Classification Search
CPC .............. G01R 33/3815; G01R 33/385; G01R 33/34007; G01R 33/3635; G01R 33/3642; G01R 33/48; G01R 33/4818; G01R 33/481; G01R 33/4824; G01R 33/446; G01R 33/4835; G01R 33/4828; G01R 33/1276
See application file for complete search history.

(56) References Cited

U.S. PATENT DOCUMENTS

| | | | |
|---|---|---|---|
| 7,778,681 B2 | 8/2010 | Gleich | |
| 8,350,566 B2 | 1/2013 | Ohyu | |
| 8,355,771 B2 | 1/2013 | Gleich | |
| 8,847,592 B2 | 9/2014 | Goodwill | |
| 9,176,206 B2 | 11/2015 | Wang | |
| 10,794,970 B2* | 10/2020 | Saha | G01R 33/34046 |
| 10,986,990 B2 | 4/2021 | Klein | |
| 11,585,882 B2* | 2/2023 | Laborde | A61K 49/1878 |
| 2008/0309330 A1 | 12/2008 | Ohyu | |
| 2009/0118611 A1* | 5/2009 | He | G01R 33/341 |
| | | | 324/322 |
| 2011/0098558 A1* | 4/2011 | Weaver | G01R 33/4808 |
| | | | 600/420 |
| 2011/0221438 A1* | 9/2011 | Goodwill | A61B 5/0515 |
| | | | 324/301 |
| 2015/0300987 A1* | 10/2015 | Rahmer | G01N 27/72 |
| | | | 324/239 |

OTHER PUBLICATIONS

Sattel, Timo "Single-sided device for magnetic particle imaging" J. Phys. D: Appl Phys. 42, 2009.
Weizenecker, J "A Simulation Study on the resolution and sensitivity of magnetic particle imaging" IOP Publishing Ltd 2007.
Cannon, Benjamin "Magnetic Resonant Coupling As a Potential Means for Wireless . . . " IEEE Transactions on Power Electronics vol. 24 No. 7, Jul. 2009.
Schulz, Volkmar; "A Field Cancellation Signal Extraction . . . "; IEEE; Feb. 1, 2015.
Weber, Matthias; "Implementation of a High-Precision 2D Receiving . . . "; IEEE; Feb. 1, 2015.

* cited by examiner

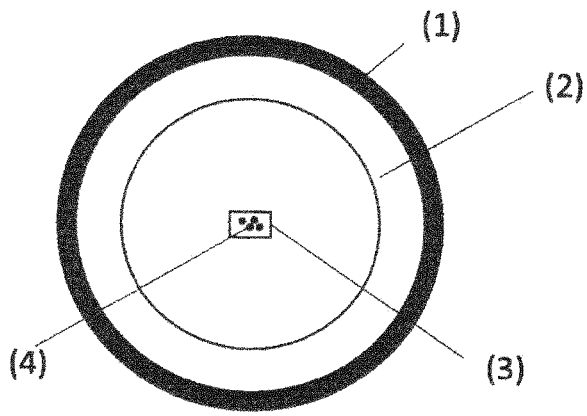
Fig. 1A - Prior Art
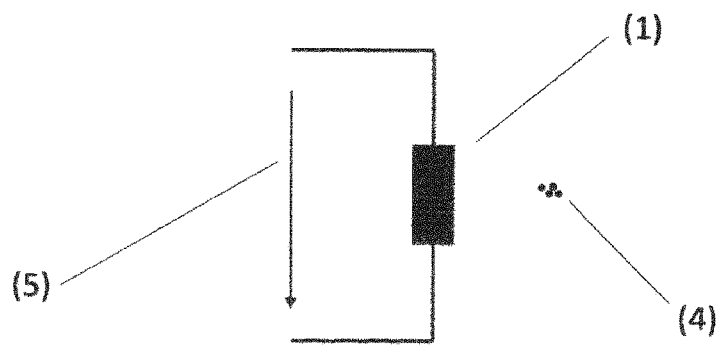
Fig. 1B - Prior Art
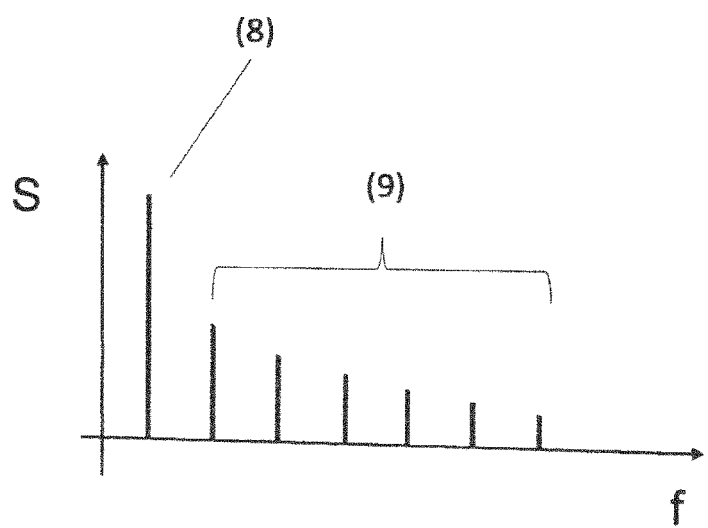
Fig. 1C - Prior Art Single Channel (z)

Single Channel (x)

Single Channel (y)

Three Channel (x,y,z)

z coils x,y coils

SIGNAL TRANSMISSION FOR MAGNETIC-PARTICLE-IMAGE SIGNAL DETECTION

CROSS REFERENCE TO RELATED APPLICATIONS

This application is the US-national stage of PCT application PCT/EP2020/056912 filed 13 Mar. 2020 and claiming the priority of German patent application 102019106665.4 itself filed 15 Mar. 2019.

BACKGROUND OF THE INVENTION

The invention relates to a method of detecting a signal with magnetic-particle imaging. The invention further relates to a signal-transmission assembly for use in such a signal detection. With the principle of magnetic particle imaging (MPI), concentrations of magnetic or at least magnetizable particles, in particular nanoparticles, such as preferably for example iron oxide, can be measured in a test space. The particles can be used, for example, as tracers, similar to a contrast agent, for tissue investigations of living beings. In particular, iron oxide has the advantage of being readily biodegradable in the organism of the living being. The technique thus represents an alternative, but at least one supplement to magnetic resonance tomography or nuclear medical methods. This test space is also referred to in the terminology of this technique as Field-Of-View (FOV).

In this fundamentally known technique, the magnetic/magnetizable particles are magnetized in the field-free region of a location-dependent magnetic field, in particular a gradient magnetic field, by a temporally changing excitation magnetic field. In this case, the excitation magnetic field that changes over time in the polarity of the field direction is superimposed with the location-dependent magnetic field.

The location-dependent magnetic field is generated, for example, by permanent magnets, but in particular also by electromagnets. The excitation magnetic field is usually generated by electromagnets, preferably by current-carrying coils that are fed by a current source in order to generate the excitation magnetic field from a temporally varying alternating currents. The location-dependent magnetic field and the varying magnetic field can also be generated in a common coil assembly. The displacement of the field-free region, defines the test space. The displacement can be effected purely mechanically, electrically or in combination.

The field-free region refers to the local region where the location-dependent magnetic field and/or the superposed location-dependent magnetic field and varying magnetic field change the field direction, that is to say is singular "zero" and furthermore, in the environment located thereabout, the field strength is below the saturation field strength of the particles used. Despite the thus successful designation, the field-free region is thus not field-free everywhere in the relevant terminology. On the other hand, signal contributions of the particles originate only from this region designated as field-free, since only there are the particles in the excitation field remagnetized.

Outside the field-free region, the magnetization of the particles is saturated and cannot be changed in the excitation magnetic field. The field-free region is in the case of conventional scanners as well as in the invention, in particular in scanners that are already commercially available, often have a line or a point, these terms not being understood in the sense of mathematical precision, but rather describing the spatial extent of a specific measurement volume. These regions are referred to in the relevant terminology as FFP (field free point) or FFL (field free line).

Due to the nonlinear magnetization of the particles, they change magnetization not only with the base frequency of the excitation magnetic field but also with the frequency of higher harmonics, in particular odd harmonics of the excitation frequency. The particles thus in turn generate alternating magnetic fields having the excitation frequency and the harmonics, and the harmonics can be discriminated in terms of measurement from the excitation frequency and thus the amplitude or intensity of the harmonics is a measure of the concentration of the particles in the field-free region.

A signal that is detected by the magnetized particles is thus usually a physical variable that represents the amplitude/intensity of the harmonics, if necessary including the excitation frequency, for example an induced voltage or further variables formed therefrom.

The technique of MPI imaging thus envisions, like this the invention, detection of the signal by a receiving coil assembly, in particular that surrounds the particles. The signal is usually detected in the time domain and converted into the frequency domain by Fourier transformation in order to measure the signal components of the harmonics.

The coil assembly, which is also used to generate the varying excitation magnetic field, as well as a separate coil assembly, can be used as the receiving coil assembly.

Known MPI scanners, for example from Bruker, comprise a sample-receiving passage that is surrounded by the coils for excitation and signal detection. Such a sample-receiving passage has a defined size that in this respect also limits the maximum size of samples that can be examined, e.g. living beings.

Frequently, investigations are made on particles in samples that are significantly smaller than the maximum diameter of the sample-receiving passage. The magnetic field strength of the harmonics generated by the particles must be detected in such devices with the receiver coil assemblies disposed externally around the sample-receiving passage. Thus, the spacing of the receiving coil assembly of the particles is larger than is actually necessary.

This is problematic because the magnetic field strength decreases significantly with the radial distance from the particles, in particular with $r^3$, as a result of which the signal yield is reduced.

In commercial MPI scanners, to reduce the spacing between the receiving coil and the particles in samples that are significantly smaller than the receiving passage diameter, a separate receiving unit with receiving coil assembly and downstream measured value detection are provided in the sample-receiving passage and then the measured value is detected with this receiving unit instead of the original receiving coil assembly and sensor of the apparatus. Such a solution entails high costs for this double measuring system.

OBJECT OF THE INVENTION

The object of the invention is thus to provide a signal-transmission method and apparatus that allow signals from the magnetized particles to be detected with a higher yield using an existing receiving coil assembly. Preferably, the measuring electronics downstream of an existing receiving coil should also be used for detecting measured values.

SUMMARY OF THE INVENTION

This object is attained by a method of the above-described type where, furthermore, a signal-transmission assembly comprising an outer and at least one inner coil connected in series is positioned around the particles within the receiving coil assembly, preferably within such a coil assembly that is present in a commercial MPI scanner.

Such a signal-transmission assembly can preferably be inserted into the sample-receiving passage as a passive component, i.e. without a further external voltage supply. As a result, the at least one inner coil can surround a sample lying in the passage at a smaller radial distance than is the case with the receiving coil assembly.

According to the invention, the signal received by the alternately magnetized particles together with the at least one inner coil is transmitted to the outer coil by current flow and is emitted again by it. Namely, the alternating magnetic field generated by the particles initially generates an induced voltage in the at least one inner coil, which voltage generates the current flow that is also produced by the outer coil connected in series and thus a magnetic field is again generated by it.

The magnetic field generated by the outer coil is in turn closer to the receiving coil in the radial direction and is again detected by it, for example as an induced voltage. Overall, the signal transmission between the particles and the receiving coil assembly can thus be improved in a purely passive manner.

The signal directly received by the particles and the signal received by the particles indirectly from the outer coil are preferably superimposed on the receiving coil assembly.

Even if the inductances of the signal-transmission assembly resulted in a time shift between the magnetic field generated by the particles and the magnetic field emitted again by the outer coil, this is not critical since, at least in the frequency domain, a constructive superposition of the harmonic signal components is received directly and indirectly.

A signal-transmission assembly according to the invention for a magnetic particle imaging scanner thus has an outer coil, in particular that is smaller in diameter than the sample-receiving passage of the existing scanner, and has at least one inner coil that is in the outer coil and is preferably coaxially therein, in particular is larger in diameter than a sample to be examined, and the outer and the inner coil are electrically connected in series. The at least one inner coil is thus always smaller in diameter than the outer coil and leaves in its interior or inside a coil support on which the at least one inner coil, a free passage-shaped cross-section of the The invention relates to a signal-transmission assembly, in which a sample with particles can be positioned.

The method and the signal-transmission assembly can, in a preferred embodiment, provide for the signal-transmission assembly to be formed by a capacitor connected in series with the outer and the inner coil and tuned in resonantly. Such a capacitor may include several actual capacitors.

Tuning can be accomplished by changing the capacitor and preferably by a capacitor whose capacitance is adjustable.

The tuning can done in that the frequency range of the harmonics to be detected is transmitted better through the coil assembly than the excitation frequency, in particular such that the excitation frequency in the coil assembly of the signal-transmission assembly is suppressed. The absorption of energy from the magnetic field at the excitation frequency can thus be reduced. The tuning can preferably take place in such a way that the selected resonance frequency is greater than the excitation frequency, preferably at least 10 times, more preferably at least 20 times greater. In an exemplary excitation frequency of the temporally varying excitation magnetic field of 25 kHz. the resonance frequency, for example to 600 kHz.

Furthermore, the capacitor is preferably located outside the excitation magnetic field. This can be realized, for example, in that the capacitor is spaced from and connected by a cable, for example by a coaxial cable or a twisted-pair line, to the coils. Even more preferably, the capacitor is in a separate shielding housing that is positioned outside the sample-receiving passage of the MPI scanner. The cable connection can preferably be at least as long as the insertion depth of the signal-transmission assembly into the sample-receiving passage.

In the signal-transmission assembly, the outer coil and the inner coil, in particular the single inner coil, can preferably be on a common coil support. The coil support can be configured in its dimensions such that its outer diameter, or the outer diameter of the entire arrangement, is smaller than a sample-receiving passage of an existing MPI scanner used with the inventive method. The inner free diameter of the signal-transmission assembly can be selected in such a way that it is larger, preferably only slightly larger, than a sample to be surrounded with the particles. The common coil support can be divided into an outer coil support for the outer coil and at least one inner coil support for a respective inner coil. The outer and inner coil supports can be integrally formed with one another or form separate coil supports, in particular that can be inserted into one another, preferably can be fastened one inside the other.

In a possible first embodiment of the respective inner and outer coils, they can in each case be a conductor winding with a pitch of the winding in the direction of the longitudinal axis. Such a respective coil thus forms an arrangement, also referred to as a solenoid, and in particular forms a cylindrical metal coil that acts like a bar magnet when current is flowing through it.

In this embodiment, in particular, the axial length of the outer coil and/or of the inner coil, preferably the number of windings of the outer and/or inner coil, preferably of the length or the inner-coil number of turns of the receiving coil assembly of the MPI scanner to be used.

However, the invention can also have different configurations of the inner and/or outer coil.

In a second possible embodiment, an inner and/or an outer coil can comprises two respective coil parts that are connected to one another in series and are opposite one another, in particular opposite one another by 180E, in particular around a longitudinal axis, preferably the longitudinal axis of the signal-transmission assembly or of the coil supports contained therein and corresponds in operation to the longitudinal axis of the sample-receiving passage. The connecting line between the center points of both coil parts can cross the longitudinal axis of the sample-receiving passage, in particular the sample volume with the particles to be analyzed.

Preferably, each of the two coil parts is a spiral winding of a conductor, the spiral winding not lying in one plane but being shaped in a plane perpendicular to the longitudinal axis, preferably partially circular. This corresponds to the idea that the coil part or the helical winding is bent around a cylindrical surface, preferably a circular cylindrical surface, and can be specifically achieved in that the spiral winding of the conductor is first made in one plane and then the formed helix is applied in a contacting manner to a cylindrical, preferably circular cylindrical surface, for example the inner and/or the outer coil support. In particular, the winding of the conductor of the respective coil part is thus a helix on a cylindrical outer-wall surface. Two such curved spirals of the conductor thus lie opposite one another, i.e. on opposite sides of the cylindrical surface. In this case, the above-mentioned center points can be the center points of the helixes. As mentioned, both coil portions are electrically connected in series with each other so as to jointly form an inner and/or outer coil.

The series circuit can preferably be such that the winding direction of both coil parts in the series circuit is the same, preferably where the part of the conductor lying centrally in the spiral in a first coil part is connected to the part of the conductor of the second coil part lying on the outside in the spiral.

In each case two such opposite coil parts form at least one inner coil and at least one outer coil that are also connected in series. The coil parts of the inner coil and the outer coil lie opposite one another in the same direction, but in particular on different cylindrical surface radii.

The opposite position of the coil parts is in a direction that is perpendicular to the longitudinal direction of the sample passage or of the coil former (inner and outer).

Such an arrangement of a coil has the advantage that the above-mentioned solenoid coils can receive signals from a first detection passage, e.g. signal contributions along the longitudinal axis of the sample passage that can be defined as the Z-axis. A coil assembly according to the opposite coil parts, signal contributions can detect in a direction perpendicular to the longitudinal axis (Z-axis) of the particles during an examination, for example the X-direction and/or Y-direction.

According to the invention, a signal-transmission assembly has an outer and at least one inner coil. These two coils can be formed either according to the above-described first embodiment or according to the above-described second embodiment. However, the invention can also provide that the signal-transmission assembly comprises inner and outer coils according to the first embodiment and additionally comprises at least one arrangement of inner and outer coils according to the above-mentioned second embodiment. Thus, signals can be detected in two or three passages.

In a further possible combined embodiment, it may be provided that the signal-transmission assembly comprises an arrangement of an outer and has at least one inner coil according to the first embodiment and two arrangements of inner and outer coils according to the second embodiment, and in the two arrangements the opposite coil parts have crossed preferably perpendicularly. Thus, one of the arrangements may, for example, comprise signals of the X direction and the other signals of the Y direction, and the solenoid coils detect signals in the Z direction.

In this case, it can be provided that, for each of the arrangements, another receiver coil assembly of the MPI scanner is used.

Overall, the invention can thus also use a three-passage signal detection.

The invention can further provide, with general validity for all possible arrangements of coils, that the inner coil is moved relative to the outer coil and relative to the particles, in particular during a signal-detection sequence. Such movement may be for example along a common axis about which the inner and outer coils are arranged. However, movement of the inner coil can also occur freely in space relative to the outer coil. Movement may also be such that the axis of the inner coil is moved parallel but not coaxial to the axis of the outer coil. Overall, the mobility of the signal detection from the particles to the inner coil can be optimized.

For example, an inner coil or its coil support can be formed for this purpose by a manually actuatable handle or also an actuator that controls the movement in space. Such a handle or actuator can also be formed, for example, by a catheter or another instrument with which the inner coil is preferably also inserted into the interior of the body of a living being to for example place it in the blood vessels thereof. This makes it possible to bring about a particularly close proximity to the particles.

In all embodiments, it is preferably provided that the outer coil and the inner coil surround the particles. In particular, it may also be provided that the inner coil does not surround the particles, but only the outer one.

In the embodiments of a movable inner coil, the latter is preferably flexibly connected to the outer coil during its electrical series connection.

One possible embodiment can provide that an inner coil support that carries the inner coil, can be moved longitudinally, preferably on the same common coil axis, to an outer coil support with the outer coil. For example, inner and outer coil supports can be connected by a linear guide system that permits straight-line movement of the bobbin supports relative to one another.

In a further development, the invention can also provide have at least two inner subcoils that are in particular spaced apart on the same axis and that can alternatively be alternately connected in series with the outer coil by a switch assembly. Each inner subcoil may have its own inner coil support carrying the coil. The inner subcoils can also be on a common inner coil support.

Thus, in the method, one of at least two inner subcoils can be used optionally for signal detection. Preferably, the two alternatively switchable subcoils are each connected in series with the same capacitor, so that the same resonance tuning is set in both subcoils, in particular if both coils are identical in terms of inductance and/or structural design. The invention can also provide that the at least two inner subcoils can each alternatively be connected in series with the same outer coil but in series with a respective capacitor. The resonance frequencies or band-pass characteristics may thus be the same for the different inner subcoils, but may also be different. The at least two alternatively switchable subcoils can also be designed differently with respect to inductance and/or construction.

The invention also provides that the signal-transmission assembly has at least two inner subcoils that are simultaneously connected in series with the same outer coil. At the same time, signals from the particles can be detected by the at least two inner subcoils, preferably that can be operated at difference resonant frequencies.

In this case, two inner subcoils can be connected in series with a common capacitor, but alternatively also in series with respective capacitors. In this case, another capacitor is to be understood as meaning such a capacitor having a different capacitance.

Preferably, the row arrangements of each inner subcoil and respective capacitor form a parallel circuit that in turn is in series with the outer coil.

The at least two inner subcoils can be identical in the inductance, but can also be of different design.

The resonance frequencies or band-pass characteristics can thus be selected for the at least two inner subcoils, in particular due to the different inductances of the subcoils and/or due to different capacities of the associated capacitors can also be designed differently.

The at least two inner subcoils of this embodiment variant can be coaxially one inside the other, in particular completely overlapping in this case, or coaxially one inside the other and axially spaced from one another or else axially spaced apart from one another, in particular on the same coil axis. The invention can be provided, for example, from the signals of the two or more, preferably axially spaced, inner subcoils, in particular of the electrically and/or structurally identical coils, to the location of the generation of the signals from the particles, in particular to improve the spatial resolution of a scanner.

A further preferred embodiment may provide that the invention relates to a signal-transmission assembly comprising a coil support having an outer coil and comprising at least one coil support having at least one inner coil that are mechanically and electrically detachable and connectable, in particular where the inner coil support having the inner coil can be selected from a set of a plurality of inner coil supports having respective inner subcoils that are different in diameter, in particular thus also different inner free diameters.

Thus, with this embodiment, depending on the sample comprising the particles, the inner coil can be selected from the set having the smallest possible diameter.

A further development can also provide that the electrical conductors of the coils can be cooled by a coolant flowed in the conductors, in particular for dissipating lost heat and/or for cooling to a superconducting resistance region. The conductors may, for example, be tubular for this purpose and integrated in a fluid circuit of a coolant, e.g. helium.

BRIEF DESCRIPTION OF THE DRAWING

The prior art and preferred embodiments are shown in the following figures.

FIG. 1A is a structural view of a prior-art MPI scanner;

FIG. 1B: shows the electrical equivalent circuit diagram for FIG. 1B;

FIG. 1C shows a prior-art signal spectrum according to FIGS. 1A and 1B as a signal amplitude against the frequency;

SPECIFIC DESCRIPTION OF THE INVENTION

Figure 2A:
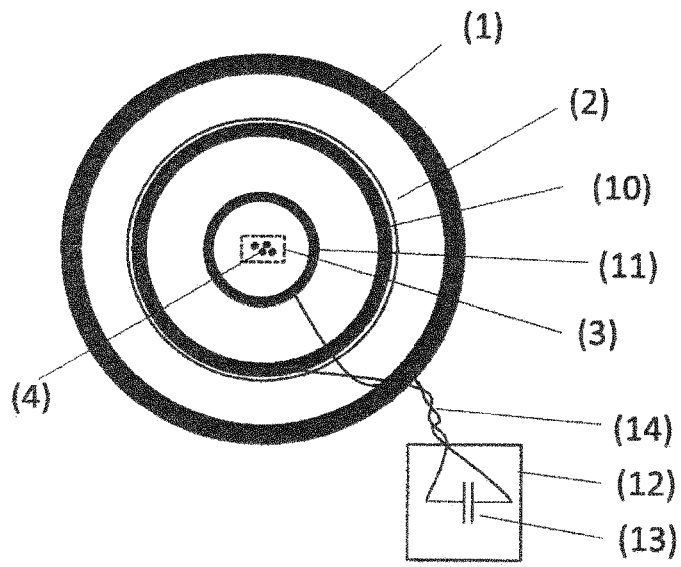
FIG. 2A is a structural view according to the invention in section perpendicular to the coil axes.
Figure 2B:
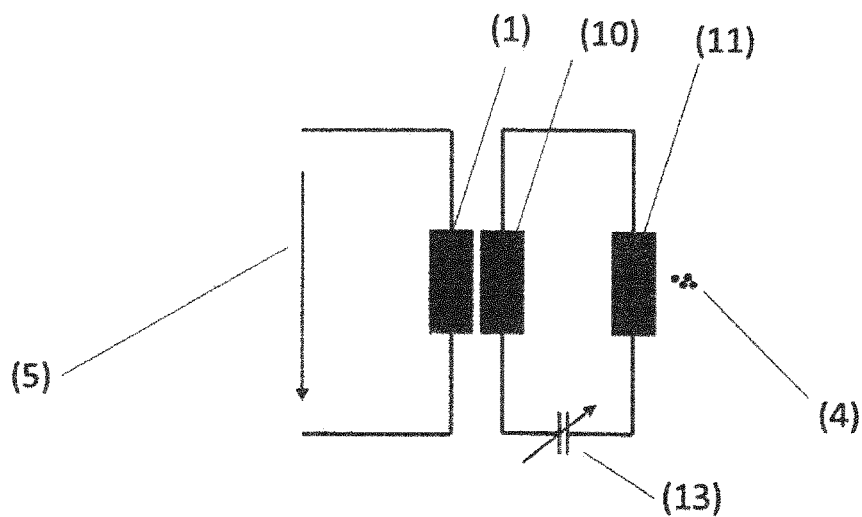
FIG. 2B shows the electrical equivalent circuit diagram of the embodiment of FIG. 2A.

An embodiment according to the prior art is shown in FIGS. 1ABC and 2ABC. In this embodiment, an exciting coil 1 driven by a driving voltage 5 generates the time-varying excitation magnetic field as well and also acts as a receiving coil to detect signals of the particles 4. The coil assembly 1 is radially outwardly surrounded by a cover 2 internally defining the sample-receiving passage. The field-free region is located in a test space 3 and in this passage can be varied locally.

The location-dependent magnetic field, in particular the gradient magnetic field, forming a field-free region is assumed here as given. The means for generating this magnetic field are not further shown or, in one possible embodiment, could also be simultaneously provided by the coil assembly 1.

As a result of the magnetic alternating field of the exciting coil 1, particles 4 in the field-free region of the test space 3 are nonlinearly remagnetized. The magnetization of the particles 4 thus changes with the base frequency of excitation and higher harmonics of this frequency. FIG. 1C shows a frequency spectrum of the measured frequencies of the alternating magnetic field generated by the particles 4. Signal components S of a base frequency/excitation frequency 8 and of the harmonics 9 that can be unambiguously assigned only to the particles 4 as the source of the signal are here plotted against frequency f.

FIG. 2ABC show a first possible embodiment of the invention. In the same way, the exciting/receiving coil 1 of a commercial MPI scanner, for example, can be seen radially behind the housing/sample-receiving passage 2.

In addition, FIG. 2ABC show a signal-transmission assembly inserted into the sample-receiving passage and also the particles 4 in the test space 3.

The signal-transmission assembly comprises an outer coil 10 that is smaller in diameter than the sample-receiving passage 2 and an inner coil 11 that is smaller in diameter than the outer coil 10, but in particular larger than a sample to be surrounded with the particles 4. Both coils 10 and 11 are electrically connected in series to one another and to a capacitor 13. In this case, the capacitor 13 that serves for resonance tuning is connected with a twisted-pair line 14 extending out of the sample-receiving passage 2 and is in a shielding housing 12. The capacitor 13 can be of fixed capacitance, but can also be adjustable, for example in that it comprises at least one rotary capacitor.

Figure 2C:
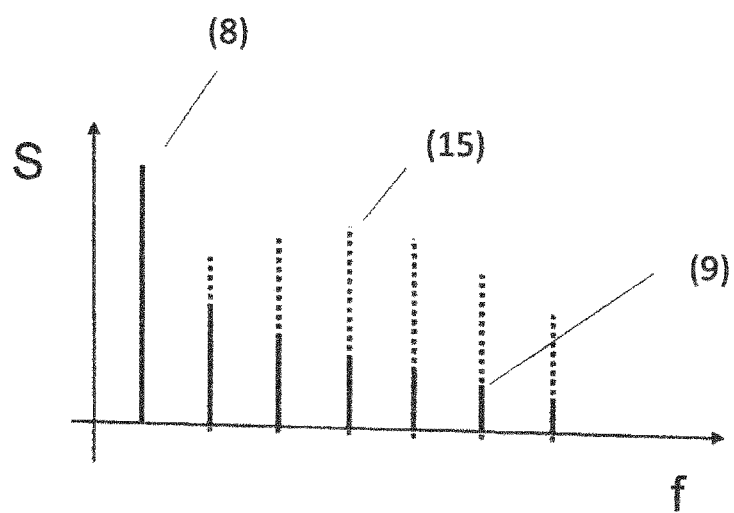
FIG. 2C shows a signal spectrum compared to the prior art according to the invention of FIG. 2A/2B with signal amplitude mapped against frequency.

FIG. 2ABC show that the inner coil 11 is closer to the particles 4 than the excitation/receiving coil assembly 1 and also closer than the outer coil 10. The magnetic field generated by the particles 4 thus induces a voltage in the inner coil 11, in particular a higher voltage than directly in the coil assembly 1. This induced voltage current to flow through the inner coil 11 and the outer coil 10, so that the latter in turn generates a magnetic field that also generates an induction voltage in the coil assembly 1. The induction voltages generated on directly and indirectly via the coils 10 and 11 in the coil assembly 1 overlap and have the same frequency components as in FIG. 1C. In contrast, FIG. 2C shows that the signal amplitude S in the harmonics 9 is increased by the signal components 15 using the invention compared to the prior art on account of the better coupling of the magnetic field generated by the particles 4 via the signal transmission device. Here, the signal components 15 increased by the invention are shown by dotted lines.

Figure 3A:
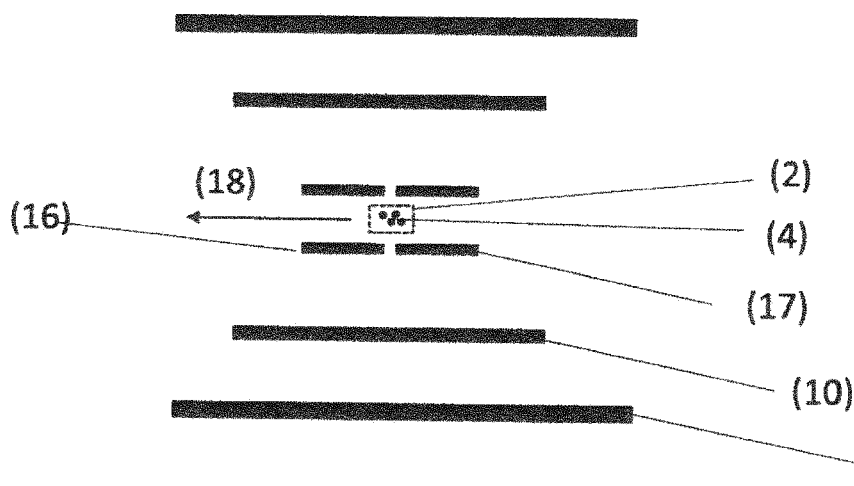
FIG. 3A is a structural view of second embodiment according to the invention in section parallel to the coil axis.
Figure 3B:
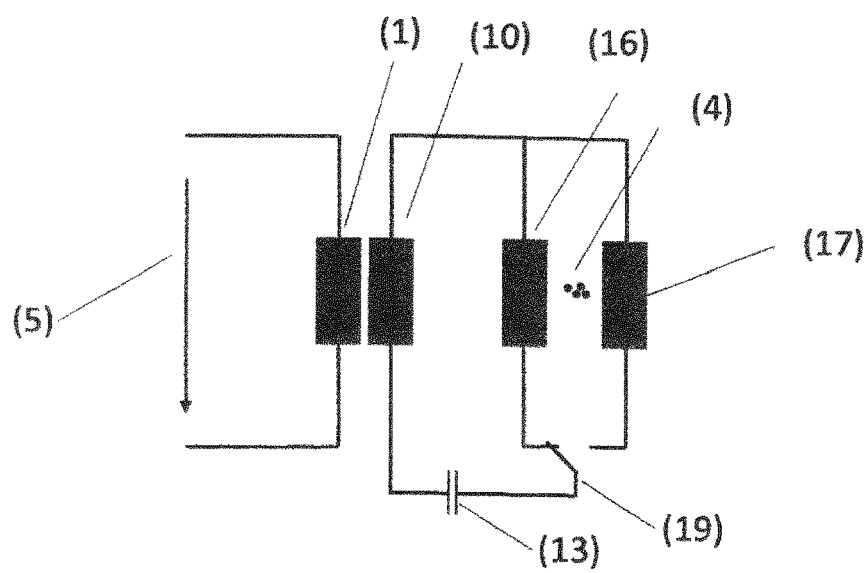
FIG. 3B: shows the electrical equivalent circuit diagram of the embodiment of FIG. 3A.

FIG. 3ABC show a further embodiment in which two inner subcoils 16 and 17 are used in the signal transmission device according to the invention. Each of the two inner subcoils 16 and 17 may alternatively be connected by a switch 19 in series with the outer coil 10 and capacitor 13.

Figure 3C:
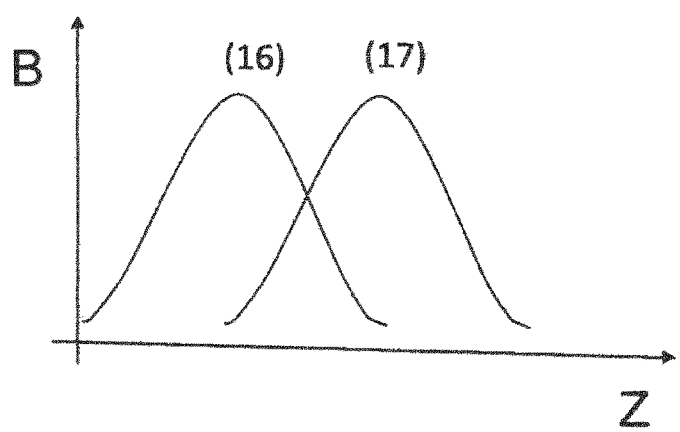
FIG. 3C shows the magnetic field strength and thus the detection sensitivity of both coils of the embodiment of FIGS. 3A-3B against the Z-axis, i.e. the coil axis.

According to FIG. 3C, two inner subcoils 16 and 17 have magnetic field strength distributions B along the coil axis Z that preferably overlap in some regions C as shown here C and that likewise form the receiving sensitivity distributions for magnetic fields generated by the particles 4 as a function of the coil axis position Z represent. On the basis of these distributions known for the coils 16 and 17, the position of the particles 4 on the coil axis Z can be inferred from the signal spectra detected on the one hand with the coil 16 and, on the other hand, with the coil 17, and thus the spatial resolution can be improved.

Instead of switching, the use of one capacitor in each case for each of the coils 16 and 17 is also possible, so that different resonance frequencies are obtained that thus make possible a simultaneous measurement.

Figure 4A:
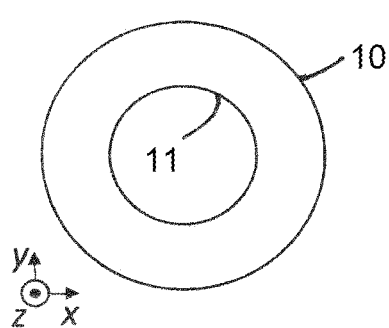
FIGS. 4A-4F show possible embodiments of the inner and outer coils of the signal-transmitting apparatus.

FIG. 4ABF show possible embodiments of the signal transmission device with regard to formation of the inner and outer coils.

Figure 4B:
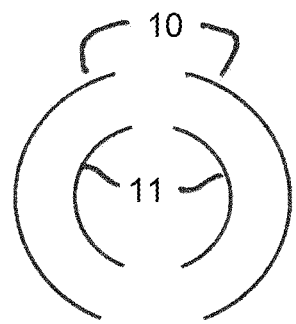
Figure 4C:
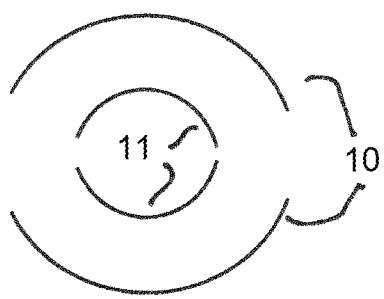

FIG. 4A shows a view of the Z-axis that is the longitudinal axis of the sample-receiving passage. The view shows the last winding position of the inner coil 11 and the outer coil 10 that are each a solenoid coil, as shown in FIG. 4E, i.e. the windings of the coil conductor extend helically about the Z-axis. In contrast, FIGS. 4B and 4C show inner and outer coils 10 and 11. The series connection of both coil parts is not shown here.

Figure 4D:
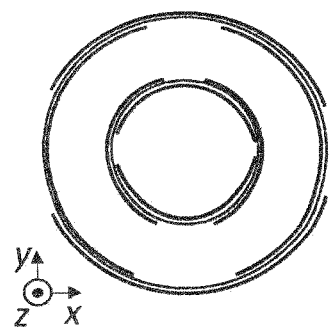
Figure 4E:
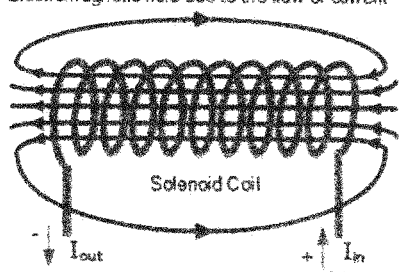
Figure 4F:
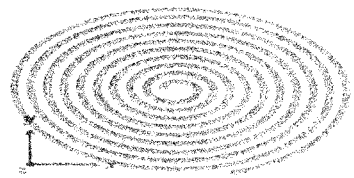

FIG. 4F shows each coil part of the two coils 10, 11 in a coplanar representation. In this illustration, the coil part is a spiral winding of the conductor. An application of this type is such however, that the spiral winding is bent, in particular bent around an imaginary or even actual cylindrical surface, for example the cylindrical surface of the inner or outer coil support that are not shown here.

The two coil parts lie diametrically opposite each other relative to the Z-axis. Thus, in the opposite position of FIG. 4C, a passage of signal detection extends in the X direction and in FIG. 4C a passage extending in the Y direction.

FIG. 4D shows a signal transmission apparatus where the coil assemblies of FIGS. 4A, B and C are jointly combined about the Z axis is shown. Signal contributions in all three directions can be detected in this arrangement.

The invention claimed is:

1. A method of detecting a signal with magnetic-particle imaging, the method comprising the steps of:
    magnetizing magnetic/magnetizable particles in a field-free region of a location-dependent magnetic field by a gradient and temporally changing excitation magnetic field;
    receiving harmonics of a frequency of an excitation magnet as signals from the magnetized particles by a receiving coil assembly surrounding the magnetized particles; and
    providing the receiving coil assembly with a signal-transmission assembly having an outer coil and at least one inner coil connected in series therewith, the coils being relatively oriented such that a signal received from the magnetized particles by the inner coil is transmitted by current flow to the outer coil and is emitted again thereby and the signal directly received by the receiving-coil assembly from the particles is superimposed on the signal received by the receiving-coil assembly from the particles indirectly from the outer coil.

2. The method according to claim 1, further comprising the step of:
    resonantly tuning the signal-transmission assembly by a capacitor assembly that is adjustable with respect to capacitance and that is connected in series with the outer coil and the inner coil to the frequency range of the harmonic while damping reception of the base frequency of the excitation magnetic field such that the capacitor is outside the excitation magnetic field.

3. The method according to claim 1, further comprising the step of:
    moving the inner coil relative to the outer coil and relative to the particles during a signal-detection sequence.

4. The method according to claim 1, further comprising the step of:
    selectively connecting one of at least two subcoils of the inner coil that are spaced from one another on the same axis in series with the outer coil by a switch assembly.

5. The method according to claim 4, further comprising the step of:
    differently tuning the inner subcoils that simultaneously receive signals from the particles.

6. A signal-transmission assembly for a magnetic particle imaging scanner/spectrometer, the assembly comprising:
    an outer coil that is smaller in diameter than a sample-receiving passage of the scanner/spectrometer;
    an inner coil that is in the outer coil coaxially therein and larger in diameter than a sample to be examined, the outer coil and the inner coil being electrically connected in series;
    a capacitor adjustable with respect to capacitance and connected in series with the outer coil and to the inner coil, the capacitor being spaced from the coils;
    a cable connecting the capacitor to the outer coil; and
    a separate shielding housing holding the capacitor.

7. The signal-transmission assembly according to claim 6, further comprising:
    a common coil support carrying the outer coil and the inner coil.

8. The signal-transmission assembly according to claim 7, wherein the inner coil is movable relative to the outer coil or to the coil support part thereof.

9. The signal-transmission assembly according to claim 6, further comprising:
    a coil support for the outer coil and
    a coil support for the inner coil that are mechanically and electrically detachable and connectable, the inner coil support being connected to the inner coil and selected from a set of a plurality of inner coil supports having inner coils that are different in diameter.

10. The signal-transmission assembly according to claim 6, wherein electrical conductors of the coils are coolable by a coolant flowed in the conductors for dissipating lost heat and/or for cooling into a superconducting range.

11. The signal-transmission assembly according to that claim 6, wherein the inner and outer coils are each wound around a longitudinal axis of a coil conductor winding with a pitch of the winding in the direction of the longitudinal axis as a solenoid coil.

12. The signal-transmission assembly according to claim 6, wherein the inner and/or the outer coil is formed by two coil parts that are connected to one another in series and are opposite one another opposite one another by 180° around a longitudinal axis.

13. The signal-transmission assembly according to claim 12, wherein each of the two coil parts is a conductor shaped as a helical winding formed in a partially circular manner in a plane perpendicular to the longitudinal axis and formed around a cylindrical surface or lies on a cylindrical surface.

14. A system comprising a magnetic-particle imaging scanner and a signal-transmission assembly according to claim 6.

15. A signal-transmission assembly for a magnetic particle imaging scanner/spectrometer, the assembly comprising:
- an outer coil that is smaller in diameter than a sample-receiving passage of the scanner/spectrometer;
- an inner coil that is in the outer coil coaxially therein and larger in diameter than a sample to be examined, the outer coil and the inner coil being electrically connected in series, each inner coil being formed by at least two inner subcoils spaced apart on the same axis and alternately connectable in series with the outer coil by a switch assembly.

16. The signal-transmission assembly according to claim 15, wherein the inner subcoils are both connected in series with the same outer coil and in series with a respective capacitor to form a respective subassembly therewith, the subassemblies being connected in parallel with each other and in series with the outer coil.

* * * * *